United States Patent
Ye et al.

(10) Patent No.: US 7,851,579 B2
(45) Date of Patent: Dec. 14, 2010

(54) CARBAZOLYL POLYMERS FOR ORGANIC ELECTRONIC DEVICES

(75) Inventors: Qing Ye, Schenectady, NY (US); Jie Liu, Niskayuna, NY (US); Kyle Erik Litz, Ballston Spa, NY (US)

(73) Assignee: General Electric Company, Niskayuna, NY (US)

( * ) Notice: Subject to any disclaimer, the term of this patent is extended or adjusted under 35 U.S.C. 154(b) by 480 days.

(21) Appl. No.: 11/764,852

(22) Filed: Jun. 19, 2007

(65) Prior Publication Data

US 2008/0135806 A1    Jun. 12, 2008

Related U.S. Application Data

(63) Continuation-in-part of application No. 11/608,924, filed on Dec. 11, 2006, now Pat. No. 7,635,777.

(51) Int. Cl.
C08G 79/00    (2006.01)
(52) U.S. Cl. .......................................... 528/9; 528/166
(58) Field of Classification Search ...................... 528/9, 528/166
See application file for complete search history.

(56) References Cited

U.S. PATENT DOCUMENTS

| | | | | |
|---|---|---|---|---|
| 2,461,901 | A * | 2/1949 | Kartaschoff | 556/108 |
| 2,630,419 | A * | 3/1953 | Wakefield et al. | 428/379 |
| 5,128,429 | A * | 7/1992 | Towle et al. | 528/9 |
| 5,777,063 | A | 7/1998 | Gordon et al. | |
| 7,060,372 | B2 * | 6/2006 | Fryd et al. | 428/690 |
| 7,396,598 | B2 * | 7/2008 | Takeuchi et al. | 428/690 |
| 2002/0103332 | A1 | 8/2002 | Leclerc et al. | |
| 2002/0182441 | A1 * | 12/2002 | Lamansky et al. | 428/690 |
| 2003/0008172 | A1 | 1/2003 | Leclerc et al. | |
| 2003/0091862 | A1 | 5/2003 | Tokito et al. | |
| 2004/0247934 | A1 * | 12/2004 | Takeuchi et al. | 428/690 |
| 2004/0260047 | A1 * | 12/2004 | Chen et al. | 528/4 |
| 2005/0116622 | A1 | 6/2005 | Lo et al. | |
| 2005/0145830 | A1 | 7/2005 | Sakakibara et al. | |
| 2005/0147843 | A1 | 7/2005 | Kobayashi et al. | |
| 2006/0003183 | A1 | 1/2006 | Helber et al. | |
| 2006/0054861 | A1 * | 3/2006 | Ionkin et al. | 252/301.16 |
| 2006/0142604 | A1 * | 6/2006 | Bach et al. | 556/146 |
| 2006/0222758 | A1 * | 10/2006 | Taka et al. | 427/66 |
| 2006/0240282 | A1 * | 10/2006 | Lin | 428/690 |
| 2007/0225464 | A1 * | 9/2007 | Lewis et al. | 528/10 |
| 2007/0231598 | A1 * | 10/2007 | Busing et al. | 428/690 |
| 2007/0281182 | A1 * | 12/2007 | Schulte et al. | 428/690 |
| 2008/0020234 | A1 * | 1/2008 | Ren et al. | 428/690 |
| 2008/0023671 | A1 * | 1/2008 | Chichak et al. | 252/301.35 |
| 2008/0023672 | A1 * | 1/2008 | Chichak et al. | 252/301.35 |
| 2008/0026249 | A1 * | 1/2008 | Chichak et al. | 428/690 |
| 2008/0026250 | A1 * | 1/2008 | Chichak et al. | 428/690 |
| 2008/0026477 | A1 * | 1/2008 | Cella et al. | 436/84 |
| 2008/0027028 | A1 * | 1/2008 | Chichak | 514/63 |
| 2008/0061686 | A1 * | 3/2008 | Liu et al. | 313/506 |
| 2008/0135806 | A1 * | 6/2008 | Ye et al. | 252/301.35 |
| 2008/0138625 | A1 * | 6/2008 | Ye et al. | 428/412 |
| 2008/0145665 | A1 | 6/2008 | Ye et al. | |
| 2008/0169756 | A1 * | 7/2008 | Son et al. | 313/504 |
| 2008/0177084 | A1 * | 7/2008 | Lee et al. | 548/444 |
| 2008/0262184 | A1 * | 10/2008 | Ye et al. | 528/9 |
| 2008/0319155 | A1 * | 12/2008 | Liu et al. | 528/125 |
| 2009/0096353 | A1 * | 4/2009 | Takahashi et al. | 313/504 |
| 2009/0118453 | A1 * | 5/2009 | Schwaiger | 528/9 |
| 2009/0156783 | A1 * | 6/2009 | Shiang et al. | 528/395 |

FOREIGN PATENT DOCUMENTS

| | | |
|---|---|---|
| JP | 61066717 | 4/1986 |
| JP | 61066718 | 4/1986 |
| JP | 2004185697 A | 7/2004 |
| WO | WO03001616 A2 | 1/2003 |
| WO | WO 2005019374 A1 * | 3/2005 |
| WO | WO2005031891 A1 | 4/2005 |

OTHER PUBLICATIONS

Brunner et al., "Carbazole Compounds as Host Materials fro Triplet Emitters in Organic Light-Emitting Diodes: Tuning the HOMO Level Without Influencing the Triplet Energy in Small Molecules", Journal of American Chemical Society, vol. 126, No. 19, pp. 6035-6042, 2004.

(Continued)

*Primary Examiner*—Vasu Jagannathan
*Assistant Examiner*—Liam J Heincer
(74) *Attorney, Agent, or Firm*—Mary Louise Gioeni

(57) ABSTRACT

Compositions comprising at least one phosphorescent organometallic compound and a polymer comprising structural units of formula II are useful in organic light emitting devices

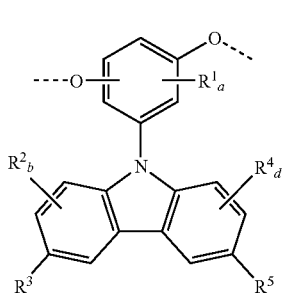

wherein $R^1$, $R^2$, and $R^4$ are independently at each occurrence a $C_1$-$C_{20}$ aliphatic radical, a $C_3$-$C_{20}$ aromatic radical, or a $C_3$-$C_{20}$ cycloaliphatic radical;

Figure 1:
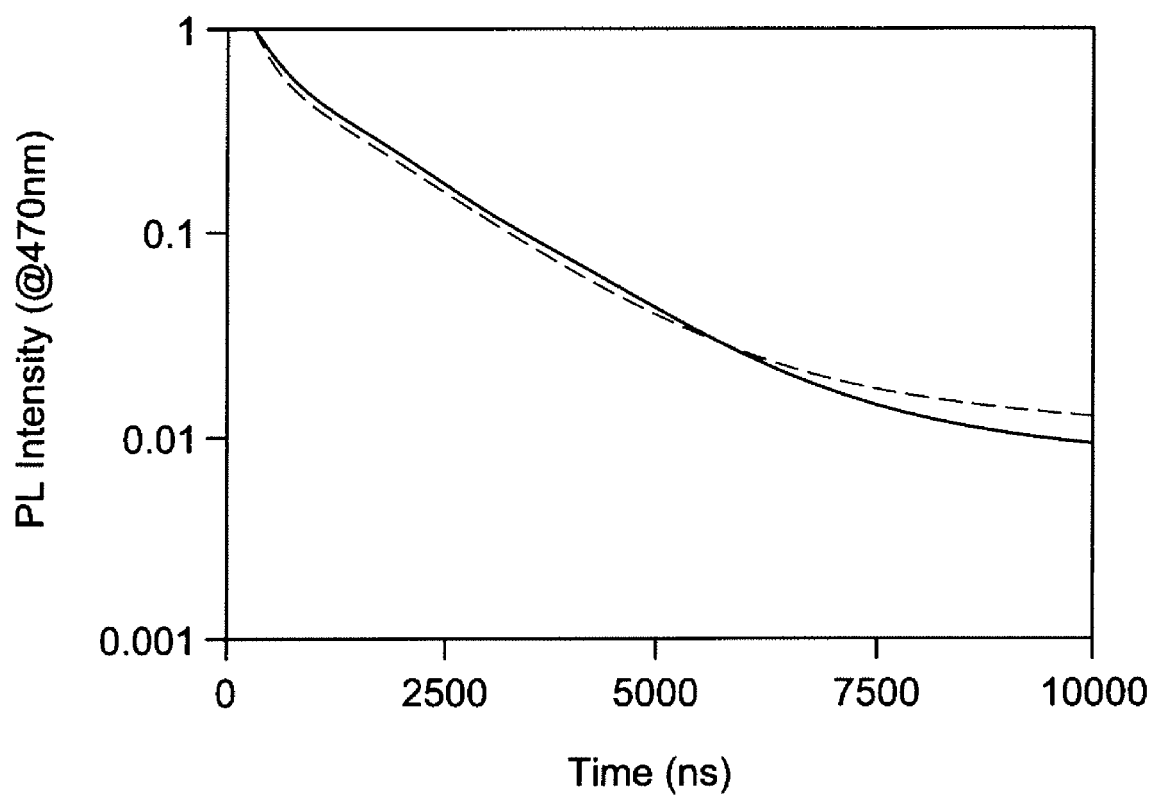

wherein $R^3$ and $R^5$ are independently selected from the group consisting of hydrogen, triphenylsilyl, t-butyl, mesityl, diphenyl phosphine oxide, and diphenyl phosphine sulfide; and a, b and d are independently 0 or an integer ranging from 1 to 3.

14 Claims, 2 Drawing Sheets

OTHER PUBLICATIONS

Burnell et al., "Synthesis and Electrooptical Properties of Copolymers Derived From Phenol-Functionalized Telechelic Oligofluorenes", Macromolecules, vol. 38, No. 26, pp. 10667-10677, 2005.

Klapars et al., "A General and Efficient Copper Catalyst for the Amidation of Aryl Halides and the N-Arylation of Nitrogen Heterocycles", Journal of American Chemical Society, vol. 123, No. 31, pp. 7727-7729, 2001.

Koene et al., "Asymmetric Triaryldiamines as Thermally Stable Hole Transporting Layers for Organic Light-Emitting Devices", Chemistry of Materials, vol. 10, No. 8, pp. 2235-2250, 1998.

Louie et al., "The Largest Discrete Oligo(m-aniline). An Exponential Growth Strategy Using Palladium-Catalyzed Amination of Aryl Sulfonates", Macromolecules, vol. 3, No. 19, pp. 6737-6739, 1998.

Yang et al., "Highly Efficient Single-Layer Polymer Electrophosphorescent Devices", Advanced Materials, vol. 16, No. 2, pp. 161-166, Jan. 16, 2004.

Hwang et al., "Synthesis and Electrochemcial and Optical Properties of Novel Poly(arylether)s with Isolated Carbazole and p-Quarterphenyl Chromophores", Macromolecules, vol. 34, No. 9, pp. 2981-2986, 2001.

Promarak et al., "Synthesis and Properties of Stable Amorphous Hole-Transporting Molecules for Electroluminescent Devices", Tetrahedron Letters, vol. 47, pp. 8949-4952, Dec. 11, 2006.

Kobayashi et al., "Novel Blue Light Emitting Poly(N-arylcarbazol-2,7-ylene) Homopolymers: Syntheses and Properties", Macromolecules, vol. 39, pp. 9102-9111, Dec. 7, 2006.

Perea et al., "Polysubstituted N-Arylcarbazoles as Discotic Molecules", Molecular Crystals and Liquid Crystals, vol. 365, pp. 695-702, 2001.

PCT International Search Report dated May 16, 2008.

Jiang et al., "Recent Advances in Organometallic Polymers as Highly Electrophosphorescent Emitters", Journal of Inorganic and Organometallic Polymers, Kluwer Publishers-Plenum Publishers, vol. 17, pp. 37-55 (Feb. 16, 2007).

Zhen et al., "Novel Light-Emitting Electrophosphorescent Copolymers Based on Carbazole with an IR Complex on the Backbone", Journal of Materials Chemistry, Royal Society of Chemistry, vol. 17, pp. 2824-2831 (Apr. 30, 2007).

PCT Search Report of Apr. 17, 2009 PCT/US2008/064093.

* cited by examiner

CARBAZOLYL POLYMERS FOR ORGANIC ELECTRONIC DEVICES

CROSS-REFERENCE TO RELATED APPLICATIONS

This application is a continuation-in-part of co-pending U.S. application Ser. No. 11/608,924, filed on 11 Dec. 2006, the entire disclosure of which is incorporated herein by reference.

BACKGROUND

The invention relates generally to compounds comprising carbazole units that are bifunctional. The invention also relates to monomers comprising carbazole units and polymers, dendrimers, and hyper-branched materials derived therefrom.

Organic light emitting devices (OLEDs), which make use of thin film materials that emit light when subjected to a voltage bias, are expected to become an increasingly popular form of flat panel display technology. This is because OLEDs have a wide variety of potential applications, including cellphones, personal digital assistants (PDAs), computer displays, informational displays in vehicles, television monitors, as well as light sources for general illumination. Due to their bright colors, wide viewing angle, compatibility with full motion video, broad temperature ranges, thin and conformable form factor, low power requirements and the potential for low cost manufacturing processes, OLEDs are seen as a future replacement technology for cathode ray tubes (CRTs) and liquid crystal displays (LCDs). Due to their high luminous efficiencies, OLEDs are seen as having the potential to replace incandescent, and perhaps even fluorescent, lamps for certain types of applications.

One approach to achieve full-color OLEDs includes energy transfer from host to emissive guest molecules. For this to be realized, the triplet energy state of the host has to be higher than the guest molecule. Carbazole derivatives have shown promise to perform well as host molecule in the presence of metal containing emissive guest molecules. Often used in this respect is poly(N-vinyl carbazole). However, quantum efficiencies of devices that use poly(N-vinyl carbazole) is still at the range of about 60 to 80%. Thus, there is a need in the art to develop OLEDs having device quantum efficiencies, while still maintaining the potential for the molecules to host red, green, and blue emissive complexes.

DRAWINGS

These and other features, aspects, and advantages of the present invention will become better understood when the following detailed description is read with reference to the accompanying drawings in which like characters represent like parts throughout the drawings, wherein:

FIG. 1 Time resolved photoluminescence spectra of device comprising polymer from Example 6 (dotted lines) and device comprising polystyrene (solid line).

Figure 2:
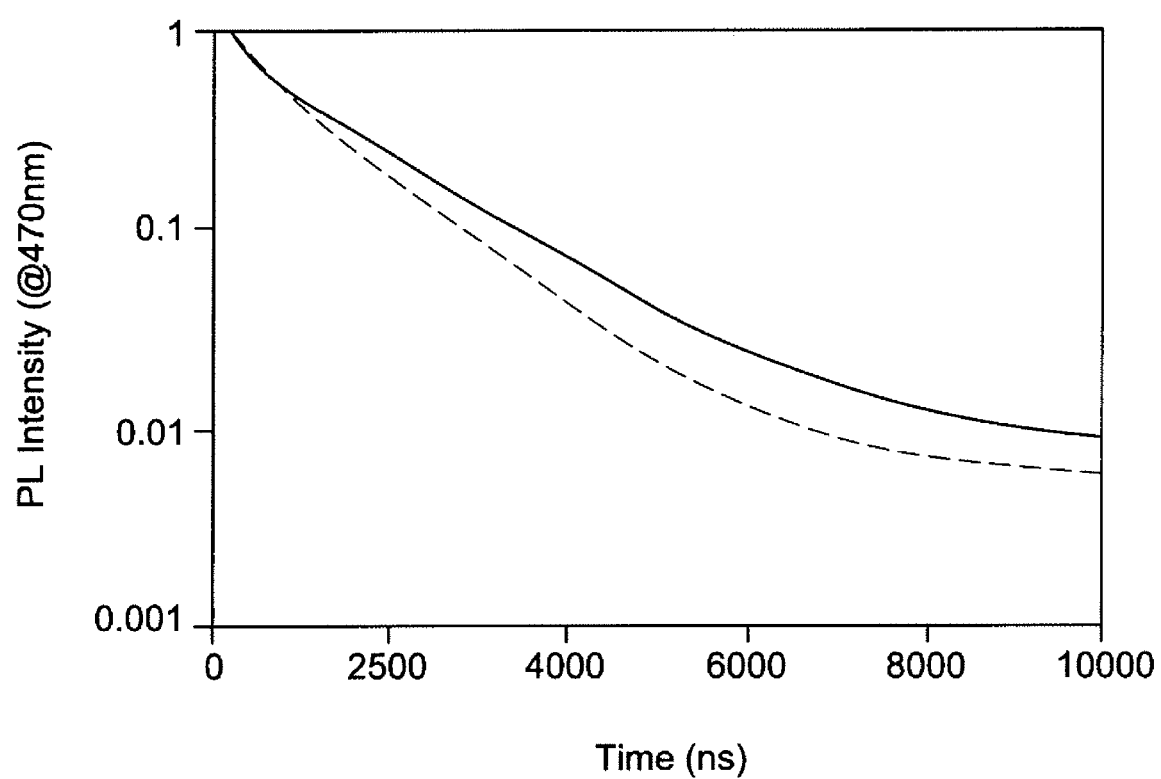

FIG. 2: Time resolved photoluminescence spectra of device comprising poly(N-vinyl carbazole) (dotted line) and device comprising polystyrene (solid line).

BRIEF DESCRIPTION

In one aspect, the present invention relates to polymers comprising structural units of formula II, and optoelectronic devices containing the polymers:

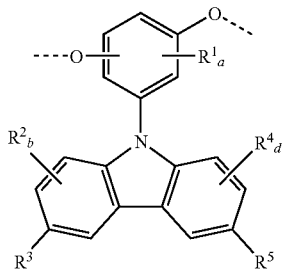

wherein $R^1$, $R^2$, and $R^4$ are independently at each occurrence a $C_1$-$C_{20}$ aliphatic radical, a $C_3$-$C_{20}$ aromatic radical, or a $C_3$-$C_{20}$ cycloaliphatic radical;

wherein $R^3$ and $R^5$ are independently selected from the group consisting of hydrogen, triphenylsilyl, t-butyl, mesityl, diphenyl phosphine oxide, and diphenyl phosphine sulfide; and a, b and d are independently 0 or an integer ranging from 1 to 3.

In another aspect, the present invention relates to a composition comprising at least one phosphorescent organometallic compound and a polymer of formula II, and optoelectronic devices containing the compositions:

In yet another aspect, the present invention relates to condensation polymers including structural units derived from a polymerizable phosphorescent organometallic compound of formula $L'_2MZ'$, and optoelectronic devices containing the condensation polymers:

wherein L' and Z' are independently bidentate ligands;

at least one of L' and Z' comprises at least one substituent selected from hydroxy, alkoxy substituted with at least one hydroxy group, aryloxy substituted with at least one hydroxy group, alkylaryloxy substituted with at least one hydroxy group, arylalkyloxy substituted with at least one hydroxy group, and combinations thereof; and M is Ga, Al, Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Ga, Ge, In, Sn, Sb, Tl, Pb, Bi, Eu, Tb, La, Po, or a combination thereof.

In yet another aspect, the present invention relates to optoelectronic devices including at least one compound of formula III or a polymer comprising structural units derived therefrom

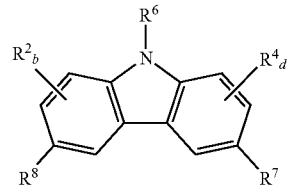

wherein $R^2$ and $R^4$ are independently $C_1$-$C_{20}$ aliphatic radical, a $C_3$-$C_{20}$ aromatic radical, or a $C_3$-$C_{20}$ cycloaliphatic radical;

$R^6$ is alkyl or substituted alkyl;

$R^7$ and $R^8$ are independently hydroxy, halo, hydroxy, alkoxy, substituted alkoxy, aryloxy, substituted aryloxy, alkylaryloxy, substituted alkylaryloxy, or a combination thereof; and b and d are independently 0 or an integer ranging from 1 to 3.

In yet another aspect, the present invention relates to optoelectronic devices including a polyester having structural units derived from phthalic acid, isothphalic acid, terephthalic acid, an ester thereof, an acid halide thereof, an anhydride thereof, or a combination thereof, preferably additionally comprising structural units derived from a hole transporting monomer, preferably a triarylamine or carbazole monomer; or from an electron transporting monomer, preferably a phenyl pyridine, a triazine, or a triazole.

DETAILED DESCRIPTION

In one aspect, the invention provides a compound of formula I

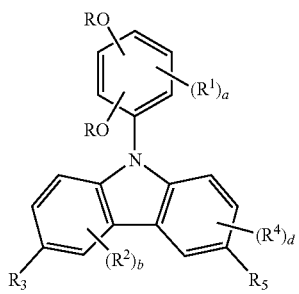

wherein R is H or alkyl; $R^1$, $R^2$, and $R^4$ are independently at each occurrence a $C_1$-$C_{20}$ aliphatic radical, a $C_3$-$C_{20}$ aromatic radical, or a $C_3$-$C_{20}$ cycloaliphatic radical; $R^3$ and $R^5$ are independently at each occurrence hydrogen, a $C_1$-$C_{20}$ aliphatic radical, a $C_3$-$C_{20}$ aromatic radical, or a $C_3$-$C_{20}$ cycloaliphatic radical; and a, b and d are independently 0 or an integer ranging from 1 to 3.

In another aspect, the invention relates to a polymer comprising structural units of formula II, where $R^1$, $R^2$, $R^3$, $R^4$, $R^5$, a, b, and c are as defined above.

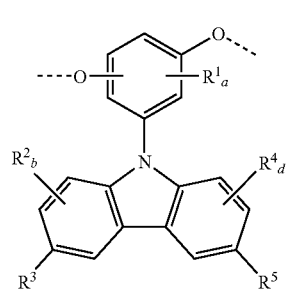

In some cases, the 3-,6-positions may be susceptible to oxidative coupling reactions, and it may be advantageous to protect one or more of these positions. Thus, in some embodiments, $R^3$ and $R^5$ are t-butyl groups, while in still other embodiments, $R^3$ and $R^5$ are trialkylsilyl and triarylsilyl groups, and in yet other embodiments, they are diphenyl phosphine oxide or diphenyl phosphine sulfide. A wide variety of other groups may also be used to substitute the carbazole at the 3- and 6-positions, and these may include, but not limited to, methyl, ethyl, methoxy, tolyl, methylcyclohexyl, and halomethyl. In a particular aspect, the invention relates to a monomer of formula I, wherein b and d are 0, which has formula

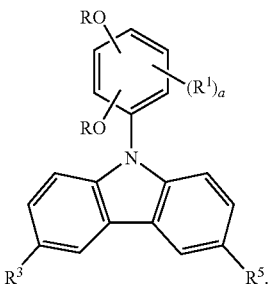

The present invention relates to carbazole compounds that are N-substituted with an aromatic group of formula

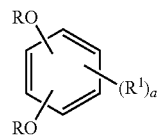

wherein R, $R^1$ and a are as defined before. The aromatic groups may be attached to the carbazole units by the reaction of an appropriate aromatic halide with carbazole to obtain the product in high yields. The reaction may be conducted in an inert solvent, and optionally, in the presence of catalysts.

In one aspect, the invention provides a compound of formula I, wherein R is an alkyl group. Thus, in one exemplary embodiment, R is a methyl group, a, b and d are all 0, the alkoxy groups are present on the 3 and 5 positions, and the resulting compound is 9-(3,5-dimethoxyphenyl)carbazole of formula

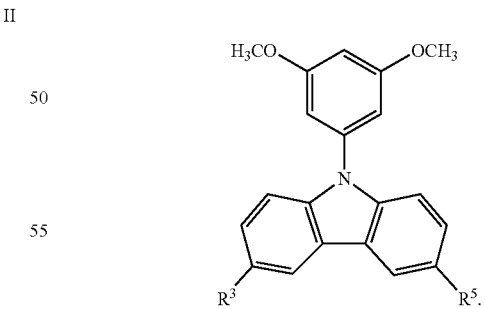

In another aspect, the invention provides a compound of formula I, wherein R is an alkyl group. Thus, in one exemplary embodiment, R is a methyl group, a, b and d are all 0, the alkoxy groups are present on the 2 and 5 positions, and the resulting compound is 9-(2,5-dimethoxyphenyl)carbazole of formula

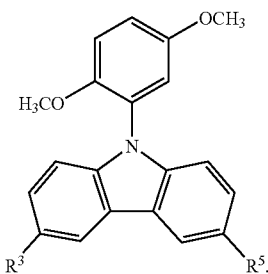

In another aspect, the invention provides a monomer of formula I, wherein R is a hydrogen, and the resulting compound is a dihydroxy functional compound. The hydroxyl groups may be present on any of the positions on the phenyl ring, for example on the 3 and 5 positions or the ortho and meta positions with respect to the position of the carbazole unit. In one particular instance, when R is a hydrogen, a, b and d are all 0, the compound is 9-(3,5-dihydroxyphenyl)carbazole of formula

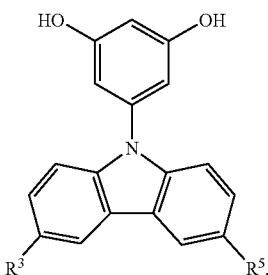

In another particular instance, when R is a hydrogen, a, b and d are all 0, the compound is 9-(2,5-dihydroxyphenyl)carbazole of formula

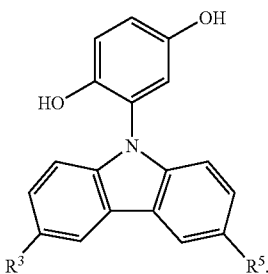

The compounds of the present invention are particularly well suited for use in hole transport layers in organic light emitting devices. In one embodiment, the present invention provides an organic light emitting device comprising a hole transport layer which consists essentially of the compounds. In another embodiment, the present invention provides an organic light emitting device comprising the compounds as a constituent of a hole transport layer of an organic light emitting device.

In another aspect, the present invention relates to polymers having structural units of formula II. The polymers are prepared by copolymerizing one or more monomers of formula I with one or more comonomers to result in polycarbonates, copolycarbonates, polyarylates, copolyarylates, copolyester-carbonates, polyethers, polyether sulfones, polyether imides, and combinations thereof, in the form of random, block, or graft copolymers, or dendrimers or hyper-branched materials.

Accordingly, in some embodiments, the monomer of formula I may be copolymerized with phosgene, or phosgene and a bisphenol, or with a diaryl carbonate or bishaloformate to provide a polycarbonate. Exemplary monomers to make polycarbonates include diphenyl carbonate, bis(methylsalicyl) carbonate, bisphenol A bischloroformate, resorcinol bischloroformate, and combinations thereof. For example, copolymerization with phosgene and bisphenol A results in a polymer comprising structural units of formula

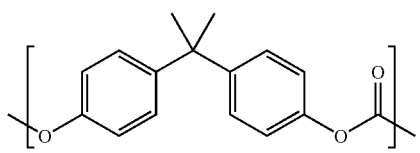

in addition to the structural units of formula II. Thus, in one particular embodiment, the resulting polymer comprises structural units of formula

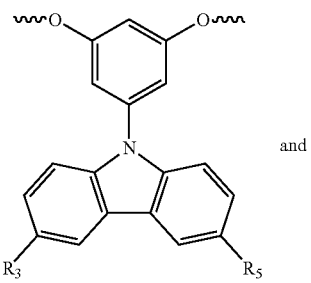

and

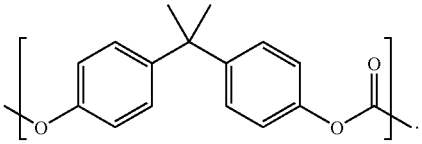

For example, a monomer of formula I may be reacted with bisphenol A and diphenyl carbonate in the presence of a minute amount of a basic catalyst such as sodium hydroxide at a temperature in a range between about 150 and 300° C. at subatmospheric pressure.

In other embodiments, the monomer of formula I may be copolymerized with a carboxylate ester, a carboxylic anhydride, or a carboxylic acid halide to yield a polyester. Exemplary comonomers that may be used to make polyesters include terephthaloyl chloride, terephthalic anhydride, naphthoic dianhydride, succinic anhydride, dimethyl oxalate, and combinations thereof.

In yet other embodiments, the monomer of formula I may be copolymerized with one or more dihaloarylsulfone monomer to yield a polyether sulfone. Dihaloarylsulfones may include bis(4-fluorophenyl)sulfone, bis(4-chlorophenyl)sulfone, 4,4'-bis((4-chlorophenyl)sulfonyl)-1,1-biphenyl and combinations thereof.

In other embodiments, the monomer of formula I may be copolymerized with one or more dihaloaryl monomers to yield a polyether. Exemplary dihaloaryl monomers include 1,6-dichlorobenzene, 4,4'-dichlorobiphenyl, 4,4'-dichlorodiphenylsulfide, 1,6-difluorobenzene, 4,4'-difluorobiphenyl, 4,4'-difluorodiphenylsulfie, and combinations thereof. For example, the monomer of formula I may be copolymerized with decafluorobiphenyl in N-methyl-2-pyrrollidone (NMP), in the presence of a base such as potassium carbonate, at the temperature between about 100 and about 250° C.

In another embodiment, the monomer of formula I may be copolymerized with dihalobenzophenone monomer to yield a polyetherketone. Other dihalobenzophenone monomers include 1,4-bis(4'-chlorobenzoyl)benzene, 1,4-bis(4'-fluorobenzoyl)benzene, 1-(4'-chlorobenzoyl-4-(4"-fluorobenzoyl)benzene, and combinations thereof. For example, the monomer of formula I together with the disodium salt of bisphenol A may be reacted with 4,4'-dichlorobenzophenone in orthodichlorobenzene at a temperature between about 100 and about 250° C. in the presence of a phase transfer catalyst such as hexaethyl guanidinium chloride.

In another embodiment, the monomer of formula I may be copolymerized with a bis(halophthalimide) such as bis(4-chlorophthalimide) to obtain a polyetherimide. Other bis(halophthalimide)s include 1,3-bis[N-(4-fluorophthalimido)] benzene, 1,4-bis[N-(4-fluorophthalimido)]benzene, 1,3-bis [N-(3-fluorophthalimido)]benzene, 1,4-bis[N-(3-fluorophthalimido)]benzene, 4,4'-bis[N-(4-fluorophthalimido)]phenyl ether, 4,4'-bis[N-(3-fluorophthalimido)]phenyl ether, 4,4'-bis[N-(4-chlorophthalimido)]phenyl ether, 4,4'-bis[N-(3-chlorophthalimido)]phenyl ether, 1,3-bis[N-(4-chlorophthalimido)]benzene, 1,4-bis[N-(4-chlorophthalimido)]benzene, 1,3-bis[N-(3-chlorophthalimido)]benzene, 1,4-bis[N-(3-chlorophthalimido)]benzene, 1-[N-(4-chlorophthalimido)]-3-[N-(3-chlorophthalimido)benzene, 1-[N-(4-chlorophthalimido)]-4-[N-(3-chlorophthalimido)benzene, and combinations thereof.

In yet another aspect, the present invention relates to compositions that include at least one phosphorescent organometallic compound and a polymer comprising structural units of formula II. In particular embodiments, the polymer may include structural units of formula

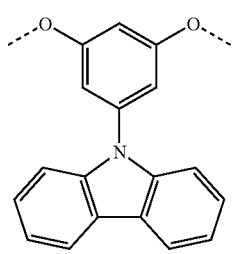

The phosphorescent organometallic compound is a compound of formula $L_2MZ$, wherein L and Z are independently bidentate ligands; and M is Ga, Al, Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Ga, Ge, In, Sn, Sb, Tl, Pb, Bi, Eu, Tb, La, Po, or a combination thereof. In some embodiments, M is iridium.

L is preferably a cyclometallated ligand. More preferably, L and Z are independently derived from phenylpyridine, tolylpyridine, benzothienylpyridine, phenylisoquinoline, dibenzoquinozaline, fluorenylpyridine, ketopyrrole, picolinate, acetylacetonate hexafluoroacetylacetonate, salicylidene, 8-hydroxyquinolinate; amino acid, salicylaldehyde, iminoacetonate, 2-(1-naphthyl)benzoxazole)), 2-phenylbenzoxazole, 2-phenylbenzothiazole, coumarin, thienylpyridine, phenylpyridine, benzothienylpyridine, 3-methoxy-2-phenylpyridine, thienylpyridine, phenylimine, vinylpyridine, pyridylnaphthalene, pyridylpyrrole, pyridylimidazole, phenylindole, derivatives thereof or combinations thereof.

In some embodiments, the phosphorescent organometallic compound is a compound of formula

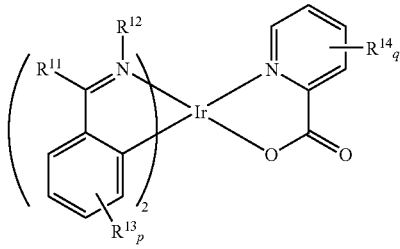

wherein $R^{11}$ and $R^{12}$ taken together form a substituted or unsubstituted monocyclic or bicyclic heteroaromatic ring; $R^{13}$ and $R^{14}$ are independently at each occurrence halo, nitro, hydroxy, amino, alkyl, aryl, arylalkyl, alkoxy, substituted alkoxy, substituted alkyl, substituted aryl, or substituted arylalkyl; p and q are independently 0, or integers ranging from 1 to 4. In particular embodiments, L is derived from a phenyl pyridine, and/or Z is derived from picolinate. In one specific embodiment, M is iridium, L is derived from 2-(4,6-difluorophenyl)pyridine, and Z is derived from picolinic acid, and the phosphorescent organometallic compound iridium(III)-bis[2-(4,6-difluorophenyl)pyridinato-N,$C^{2'}$]picolinate (FIrpic), which is a commercially available blue phosphorescent dye.

In various embodiments, the phosphorescent dye may be a red phosphorescent dye, a green phosphorescent dye, or a blue phosphorescent dye. An exemplary blue phosphorescent dye, other than FIrpic, is

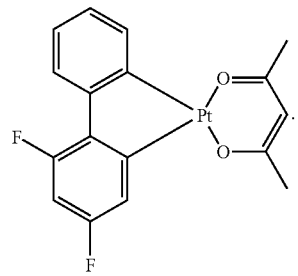

Exemplary green phosphorescent dyes include:

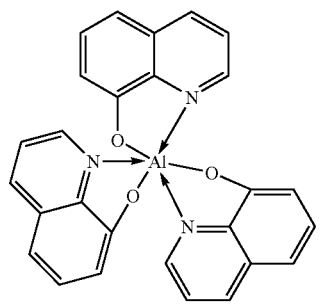

-continued

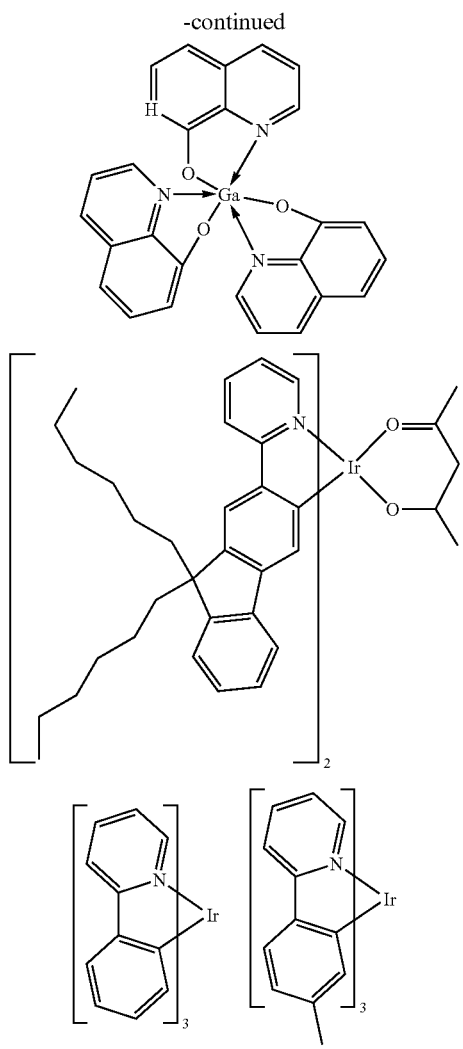
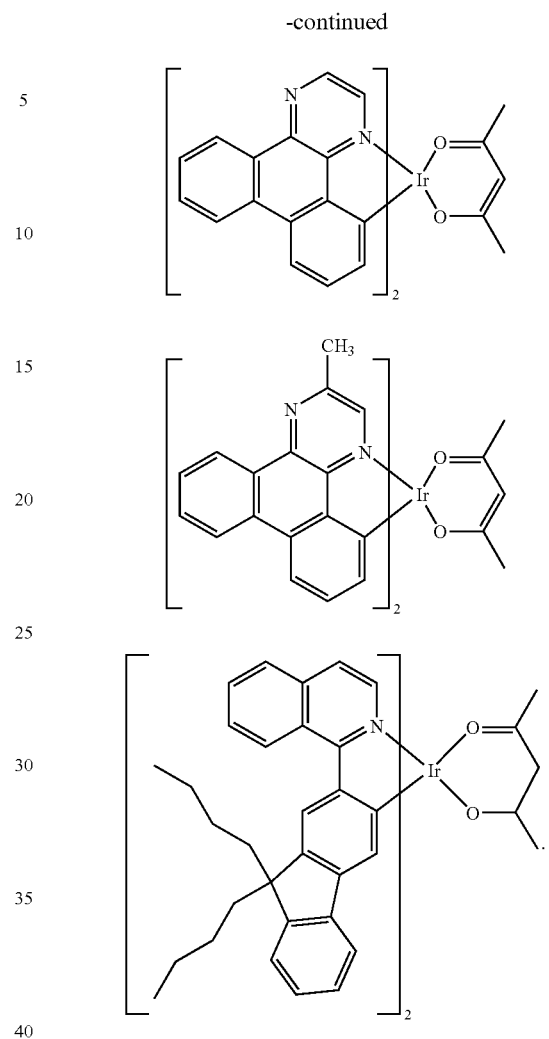

Exemplary red phosphorescent dyes include:

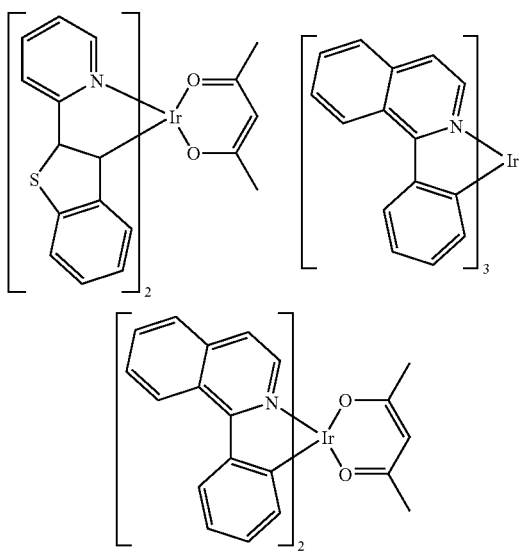

Phosphorescent organometallic compounds as described herein, may be synthesized by methods known in the art. Alternately, the phosphorescent organometallic compounds of the invention may be obtained from commercial sources, such as American Dye Sources, Quebec, Canada.

The phosphorescent organometallic compound may be present in the compositions of the present invention in an amount ranging from about 0.01 mole percent to about 25 mole percent with respect to the number of moles of the structural unit derived from the monomer of formula I. In particular embodiments, the phosphorescent organometallic compound may be present in an amount ranging from about 0.1 mole percent to about 10 mole percent. Alternately, the amount of the organometallic compound may be expressed as weight percent of the total weight of the polymer; in such cases, the amount of the organometallic compound ranges from about 0.1 weight percent to about 40 weight percent.

In another aspect, the present invention relates to condensation polymers that include structural units derived from a polymerizable phosphorescent organometallic compound of formula L'$_2$MZ', wherein L' and Z' are independently bidentate ligands; at least one of L' and Z' comprises at least one substituent selected from hydroxy, alkoxy substituted with at least one hydroxy group, aryloxy substituted with at least one hydroxy group, alkylaryloxy substituted with at least one hydroxy group, arylalkyloxy substituted with at least one hydroxy group, and combinations thereof; and M is Ga, Al, Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Ga, Ge, In, Sn, Sb, Tl, Pb, Bi, Eu, Tb, La, Po, or a combination thereof. In the context of the present invention, a condensation polymer is a polymer formed through a condensation reaction in which two molecules or moieties combine to form a single molecule, together with the loss of a small molecule, such as water, hydrogen chloride, methanol, or acetic acid. Condensation polymers are distinct from addition polymers which involve the reaction of unsaturated monomers. Condensation polymers according to the present invention include, but are not limited to, polyesters, polyester, polycarbonates, polyethers, polyetherimides, polyaryletherketones, polyarylethersulfones and polyestercarbonates, preferably polyesters.

Preferably, M is Tc, Ru, Rh, Pd, Re, Os, Ir, Pt, or a combination thereof. More preferably, M is Ru, Pd, Os, Ir, Pt, or a combination thereof. Most prefereably, M is Ir and the polymerizable phosphorescent organometallic compound is an organic iridium composition.

Preferably, L' is a cyclometallated ligand. More preferably, L' and Z' are independently derived from phenylpyridine, tolylpyridine, benzothienylpyridine, phenylisoquinoline, dibenzoquinozaline, fluorenylpyridine, ketopyrrole, picolinate, acetylacetonate, hexafluoroacetylacetonate, salicylidene, 8-hydroxyquinolinate; amino acid, salicylaldehyde, iminoacetonate, 2-(1-naphthyl)benzoxazole)), 2-phenylbenzoxazole, 2-phenylbenzothiazole, coumarin, thienylpyridine, phenylpyridine, benzothienylpyridine, 3-methoxy-2-phenylpyridine, thienylpyridine, phenylimine, vinylpyridine, pyridylnaphthalene, pyridylpyrrole, pyridylimidazole, phenylindole, derivatives thereof or combinations thereof. In some other specific embodiments, L' is derived from 1-phenylisoquinoline, 2-phenylpyridine, a derivative thereof, or a combination thereof.

In particular, the polymerizable organometallic compound may be a compound of formula

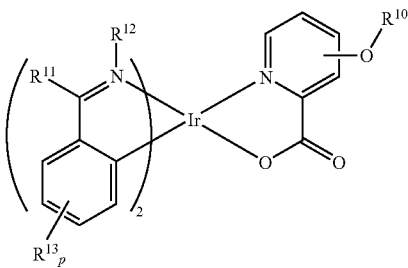

wherein $R^{10}$ is hydrogen, alkoxy substituted with at least one hydroxy group, aryl substituted with at least one hydroxy group, alkylaryl substituted with at least one hydroxy group, arylalkyl substituted with at least one hydroxy group, or a combination thereof; $R^{11}$ and $R^{12}$ taken together form a substituted or unsubstituted monocyclic or bicyclic heteroaromatic ring; $R^{13}$ is independently at each occurrence halo, nitro, hydroxy, amino, alkyl, aryl, arylalkyl, alkoxy, substituted alkoxy, substituted alkyl, substituted aryl, or substituted arylalkyl; and p is 0, or is an integer that ranges from 1 to 4.

In particular embodiments, L' is derived from a phenyl pyridine, and/or Z' is derived from picolinate, and comprises at least one substituent selected from hydroxy, alkoxy substituted with at least one hydroxy group, aryl substituted with at least one hydroxy group, alkylaryl substituted with at least one hydroxy group, arylalkyl substituted with at least one hydroxy group. In one specific embodiment, M is iridium, L is derived from 2-(4,6-difluorophenyl)pyridine, and Z is derived from a hydroxypicolinic acid, and the polymerizable phosphorescent organometallic compound is FIrpic. An exemplary embodiment of a condensation polymer according to the present invention is a polymer of formula

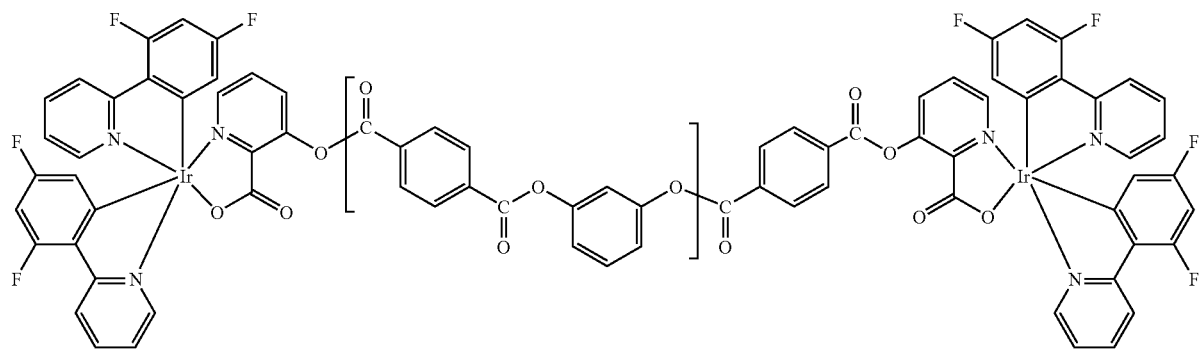

wherein the group shown in parentheses is a repeating group.

In addition to structural units derived from a polymerizable organometallic compound, condensation polymers according to the present invention may additionally include structural units of formula II, particularly structural units of formula

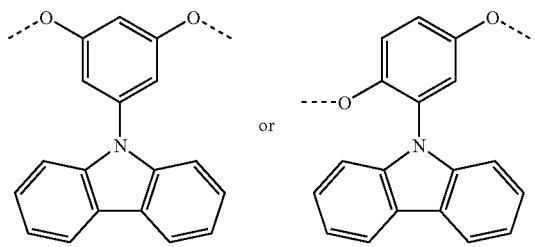

and structural units of formula

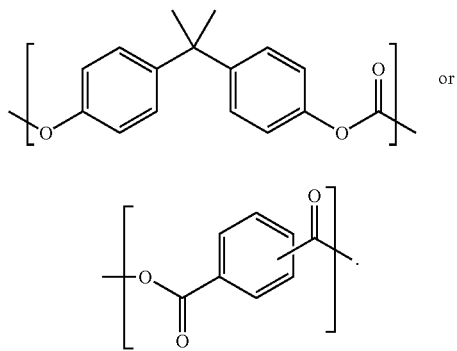

An exemplary embodiment of a condensation polymer according to the present invention is a polymer of formula Polymerizable phosphorescent organometallic compounds of the invention may be prepared in a multistep process. For example, a first intermediate may be prepared by heating a ligand precursor, such as 2-(4,6-difluorophenyl)pyridine, with metal halide, such as $IrCl_3$, in the presence of a solvent such as aqueous 2-methoxyethanol, to afford the chloride-bridged cyclometallated iridium dimer intermediate (e.g. $\{(Fppy)_2Ir(\mu-Cl)\}_2$). The chloride-bridged cyclometallated iridium dimer intermediate may be reacted with a functionalized ancillary ligand such as 4-hydroxy picolinic acid, in the presence of a base to afford the corresponding functionalized organic iridium complex. Subsequently, the organic iridium complex is reacted with a suitable organic reactant comprising a vinyl group and a functional group that can react with the functionalized organic iridium complex to provide the polymerizable phosphorescent organometallic compound. Some of the intermediates described herein may also be available from commercial sources, such as Aldrich Chemical Company, Milwaukee, Wis., or American Dye Sources, Quebec, Canada.

The polymerizable phosphorescent organometallic compound may be present in an amount ranging from about 0.1 mole percent to about 25 mole percent with respect to the total number of moles of the monomer of formula I, preferably about 1 mole percent to about 10 mole percent.

The polymerization reaction may be controlled the addition of a suitable monofunctional reactant, sometimes also referred to in the art as "end-capping agents", or "chain stoppers". The chain stopper serves to limit polymer molecular weight. Suitable phenolic chain stoppers include phenol, p-cumylphenol, and the like. Suitable aromatic halide chain stoppers include, 4-chlorophenyl phenyl sulfone, 4-fluorophenyl phenyl sulfone, 4-chlorophenyl phenyl ketone, and the like.

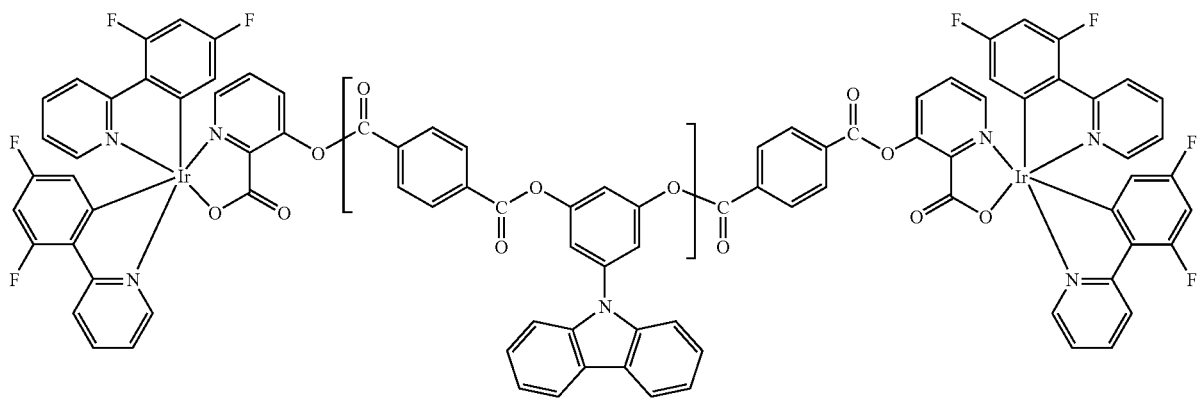

wherein the group shown in parentheses is a repeating group.

In yet another aspect, the present invention relates to optoelectronic devices including at least one compound of formula III or a polymer comprising structural units derived therefrom

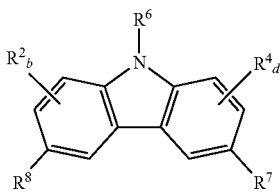

wherein $R^2$ and $R^4$ are independently $C_1$-$C_{20}$ aliphatic radical, a $C_3$-$C_{20}$ aromatic radical, or a $C_3$-$C_{20}$ cycloaliphatic radical;

$R^6$ is alkyl or substituted alkyl;

$R^7$ and $R^8$ are independently hydroxy, halo, hydroxy, alkoxy, substituted alkoxy, aryloxy, substituted aryloxy, alkylaryloxy, substituted alkylaryloxy, or a combination thereof; and b and d are independently 0 or an integer ranging from 1 to 3.

In a particular embodiment, the compound of formula III is

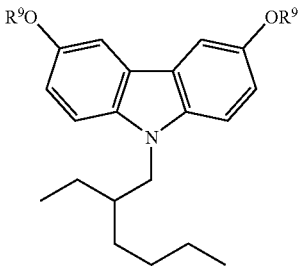

and $R^9$ is H or methyl.

In yet another aspect, the present invention relates to optoelectronic devices that include a polyester having structural units derived from phthalic acid, isothphalic acid, terephthalic acid, an ester thereof, an acid halide thereof, an anhydride thereof, or a combination thereof. The polyester may be present in a hole transporting layer, an electron transporting layer, and/or an emissive layer. The polyester may additionally include structural units derived from a hole transporting monomer, for example, triarylamines or carbazoles, or an electron transporting monomer, for example, phenyl pyridines, triazines, or triazoles. Solubility of polyesters for use in optoelectronic devices of the present invention may be adjusted by varying the polymer composition to allow sequential application of electroactive layers by solution processes. Compatible electroactive organic materials and solvents for use in constructed a multilayered device may be selected according to the methods taught in US Patent Application 20050136285. In particular, the polyester composition may be varied to result in differential solubility by changing the ratio of terephthalic to isothphalic and/or phthalic co-monomers. For example, if only terephthalic co-monomers are used, the resulting polymers typically have limited solubility in common organic solvents such as hexane, toluene, xylene, methylene chloride, and chlorobenzene, and are soluble in perfluorinated solvents such as, 1,1,3,3,3-hexafluoro-2-propanol (HFIP), or solvent mixtures containing HFIP. Polyesters containing terephthalic co-monomer and isothphalic co-monomer typically have a broader solubility window, and may be soluble in chlorinated solvents, such as methylene chloride.

Compositions and polymers provided in the present invention may find use in a wide variety of applications that include, but are not limited to, light emitting electrochemical cells, photo detectors, photo conductive cells, photo switches, and display devices. Thus, in one aspect, the invention provides a light emitting device comprising at least one electrode, at least one hole injection layer, at least one light emissive layer; wherein the light emissive layer comprises a composition comprising at least one phosphorescent organometallic compound and at least one polymer having structural units derived from at least one monomer of formula I. In another aspect, the invention provides a light emitting comprising at least one electrode, at least one hole injection layer, at least one light emissive layer; wherein the light emissive layer comprises a composition comprising at least one polymer having structural units derived from at least one monomer of formula I and structural units derived from a polymerizable phosphorescent organometallic compound.

The compositions of the present invention are particularly well suited for use in an electroactive layers in organic light emitting devices. In one embodiment, the present invention provides an organic light emitting device comprising an electroactive layer which consists essentially of a composition or polymer of the invention. In another embodiment, the present invention provides an organic light emitting device comprising the composition or polymer of the invention as a constituent of an electroactive layer of an organic light emitting device. In one embodiment, the present invention provides an organic light emitting device comprising the composition or polymer of the invention as a constituent of a light emitting electroactive layer of an organic light emitting device.

Reaction conditions useful for the preparation of the polymer compositions provided by the present invention include the use of polar solvents and bases of suitable strength. Exemplary solvents include chloroform, methylene chloride, orthodichlorobenzene, veratrole, anisole, and the like, and combinations thereof. Exemplary bases include triethylamine, sodium hydroxide, potassium hydroxide, and the like, and combinations thereof. Suitable catalysts may also be employed to effect the polymerization reaction.

In certain embodiments, the polymerization reaction may be conducted at a suitable temperature that ranges from about room temperature to about the boiling point of the solvent of choice. The polymerization may also be conducted at atmospheric pressure, subatmospheric pressures, or superatmospheric pressures. The polymerization reaction is conducted for a time period necessary to achieve polymer of a suitable molecular weight. The molecular weight of a polymer is determined by any of the techniques known to those skilled in the art, and include viscosity measurements, light scattering, osmometry, and the like. The molecular weight of a polymer is typically represented as a number average molecular weight $M_n$, or weight average molecular weight, $M_w$. A particularly useful technique to determine molecular weight averages is gel permeation chromatography (GPC), from wherein both number average and weight average molecular weights are obtained. In some embodiments, polymers of $M_w$ greater than 30,000 grams per mole (g/mol) is desirable, in other embodiments, polymers of $M_w$ greater than 50,000 g/mol is desirable, while in yet other embodiments, polymer of $M_w$ greater than 80,000 g/mol is desirable.

Polymers provided in the present invention may find use in a wide variety of applications that include, but are not limited to, light emitting electrochemical cells, photo detectors, photo conductive cells, photo switches, display devices and the like. Thus, in one aspect, the invention provides a light emitting comprising at least one electrode, at least one hole injection layer, at least one light emissive layer; wherein the light emissive layer comprises a polymer comprising structural units of formula II.

The polymer compositions of the present invention are particularly well suited for use in an electroactive layers in organic light emitting devices. In one embodiment, the present invention provides an organic light emitting device comprising an electroactive layer which consists essentially of the polymer compositions. In another embodiment, the present invention provides an organic light emitting device comprising the polymer compositions as a constituent of an electroactive layer of an organic light emitting device. In one embodiment, the present invention provides an organic light emitting device comprising the polymer compositions as a constituent of a light emitting electroactive layer of an organic light emitting device.

An organic light emitting device typically comprises multiple layers which include in the simplest case, an anode layer and a corresponding cathode layer with an organic electroluminescent layer disposed between said anode and said cathode. When a voltage bias is applied across the electrodes, electrons are injected by the cathode into the electroluminescent layer while electrons are removed from (or "holes" are "injected" into) the electroluminescent layer from the anode. Light emission occurs as holes combine with electrons within the electroluminescent layer to form singlet or triplet excitons, light emission occurring as singlet excitons transfer energy to the environment by radiative decay.

Other components which may be present in an organic light emitting device I addition to the anode, cathode, and light emitting material include hole injection layers, electron injection layers, and electron transport laers. The electron transport layer need not be in contact with the cathode, and frequently the electron transport layer is not an efficient hole transporter and thus it serves to block holes migrating toward the cathode. During operation of an organic light emitting device comprising an electron transport layer, the majority of charge carriers (i.e. holes and electrons) present in the electron transport layer are electrons and light emission can occur through recombination of holes and electrons present in the electron transport layer. Additional components which may be present in an organic light emitting device include hole transport layers, hole transporting emission (emitting) layers and electron transporting emission (emitting) layers.

Compounds of formula I have triplet energy states that are useful in applications such as organic light emitting devices (OLEDs), as they may give rise to highly efficient devices. Further, the triplet energy of these compounds may be high enough that it may be greater than those of guest dyes used in devices, and thus may serve as host molecules. The compounds of the present invention are particularly well suited for use in hole transport layers in organic light emitting devices. In one embodiment, the present invention relates to an organic light emitting device comprising the compounds as a constituent of a hole transport layer of an organic light emitting device.

The organic electroluminescent layer is a layer within an organic light emitting device which when in operation contains a significant concentration of both electrons and holes and provides sites for exciton formation and light emission. A hole injection layer is a layer in contact with the anode which promotes the injection of holes from the anode into the interior layers of the OLED; and an electron injection layer is a layer in contact with the cathode that promotes the injection of electrons from the cathode into the OLED; an electron transport layer is a layer which facilitates conduction of electrons from cathode to a charge recombination site. The electron transport layer need not be in contact with the cathode, and frequently the electron transport layer is not an efficient hole transporter and thus it serves to block holes migrating toward the cathode. During operation of an organic light emitting device comprising an electron transport layer, the majority of charge carriers (i.e. holes and electrons) present in the electron transport layer are electrons and light emission can occur through recombination of holes and electrons present in the electron transport layer. A hole transport layer is a layer which when the OLED is in operation facilitates conduction of holes from the anode to charge recombination sites and which need not be in contact with the anode. A hole transporting emission layer is a layer in which when the OLED is in operation facilitates the conduction of holes to charge recombination sites, and in which the majority of charge carriers are holes, and in which emission occurs not only through recombination with residual electrons, but also through the transfer of energy from a charge recombination zone elsewhere in the device. An electron transporting emission layer is a layer in which when the OLED is in operation facilitates the conduction of electrons to charge recombination sites, and in which the majority of charge carriers are electrons, and in which emission occurs not only through recombination with residual holes, but also through the transfer of energy from a charge recombination zone elsewhere in the device.

Materials suitable for use as the anode include materials having a bulk conductivity of at least about 100 ohms per square, as measured by a four-point probe technique. Indium tin oxide (ITO) is frequently used as the anode because it is substantially transparent to light transmission and thus facilitates the escape of light emitted from electro-active organic layer. Other materials which may be utilized as the anode layer include tin oxide, indium oxide, zinc oxide, indium zinc oxide, zinc indium tin oxide, antimony oxide, and mixtures thereof.

Materials suitable for use as the cathode include by zero valent metals which can inject negative charge carriers (electrons) into the inner layer(s) of the OLED. Various zero valent metals suitable for use as the cathode 20 include K, Li, Na, Cs, Mg, Ca, Sr, Ba, Al, Ag, Au, In, Sn, Zn, Zr, Sc, Y, elements of the lanthamide series, alloys thereof, and mixtures thereof. Suitable alloy materials for use as the cathode layer include Ag—Mg, Al—Li, In—Mg, Al—Ca, and Al—Au alloys. Layered non-alloy structures may also be employed in the cathode, such as a thin layer of a metal such as calcium, or a metal fluoride, such as LiF, covered by a thicker layer of a zero valent metal, such as aluminum or silver. In particular, the cathode may be composed of a single zero valent metal, and especially of aluminum metal.

Light emitting devices according to the present invention include polymers having formula II in the hole injection layer. The polymers may be used in place of, or in addition to traditional materials such as poly(3,4-ethylenedioxythiophene), which is commercially available from H.C. Stark, Inc. under the BAYTRON® tradename, and polymers based on the thieno[3,4b]thiophene (TT) monomer, commercially available from Air Products Corporation. In particular, the polymers may be blended with PEDOT to form a hole injection layer.

Materials suitable for use in hole transporting layers include 1,1-bis((di-4-tolylamino)phenyl)cyclohexane, N,N'-bis(4-methylphenyl)-N,N'-bis(4-ethylphenyl)-(1,1'-(3,3'-dimethyl)biphenyl)-4,4'-diamine, tetrakis-(3-methylphenyl)-N,N,N',N'-2,5-phenylenediamine, phenyl-4-N,N-diphenylaminostyrene, p-(diethylamino) benzaldehyde diphenylhydrazone, triphenylamine, 1-phenyl-3-(p-(diethylamino) styryl)-5-(p-(diethylamino)phenyl)pyrazoline, 1,2-trans-bis(9H-carbazol-9-yl)cyclobutane, N,N,N',N'-tetrakis(4-methylphenyl)-(1,1'-biphenyl)-4,4'-diamine, copper phthalocyanine, polyvinylcarbazole, (phenylmethyl)polysilane; poly(3,4-ethylendioxythiophene) (PEDOT), polyaniline, polyvinylcarbazole, triaryldiamine, tetraphenyldiamine, aromatic tertiary amines, hydrazone derivatives, carbazole derivatives, triazole derivatives, imidazole derivatives, oxadiazole derivatives having an amino group, and polythiophenes as disclosed in U.S. Pat. No. 6,023,371.

Materials suitable for use as the electron transport layer include poly(9,9-dioctyl fluorene), tris(8-hydroxyquinolato) aluminum ($Alq_3$), 2,9-dimethyl-4,7-diphenyl-1,1-phenanthroline, 4,7-diphenyl-1,10-phenanthroline, 2-(4-biphenylyl)-5-(4-t-butylphenyl)-1,3,4-oxadiazole, 3-(4-biphenylyl)-4-phenyl-5-(4-t-butylphenyl)-1,2,4-triazole, 1,3,4-oxadiazole-containing polymers, 1,3,4-triazole-containing polymers, quinoxaline-containing polymers, and cyano-PPV.

Materials suitable for use in the light emitting layer include electroluminescent polymers such as poly(9,9-dioctyl fluorene) and copolymers thereof, such as F8-TFB.

In one aspect, polymers comprising structural units of formula II may form part of the hole collection layer, while in another aspect, polymers comprising structural units of formula II form part of the hole injection layer. Thus, in one aspect, the present invention relates to more efficient organic light emitting devices comprising polymers comprising structural units of formula II.

DEFINITIONS

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having $4n+2$ "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehydes groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —$OPhC(CF_3)_2PhO$—), 4-chloromethylphen-1-yl, 3-trifluorovinyl-2-thienyl, 3-trichloromethylphen-1-yl (i.e., 3-$CCl_3Ph$—), 4-(3-bromoprop-1-yl)phen-1-yl (i.e., 4-$BrCH_2CH_2CH_2Ph$—), and the like. Further examples of aromatic radicals include 4-allyloxyphen-1-oxy, 4-aminophen-1-yl (i.e., 4-$H_2NPh$—), 3-aminocarbonylphen-1-yl (i.e., $NH_2COPh$—), 4-benzoylphen-1-yl, dicyanomethylidenebis(4-phen-1-yloxy) (i.e., —$OPhC(CN)_2PhO$—), 3-methylphen-1-yl, methylenebis(4-phen-1-yloxy) (i.e., —$OPhCH_2PhO$—), 2-ethylphen-1-yl, phenylethenyl, 3-formyl-2-thienyl, 2-hexyl-5-furanyl, hexamethylene-1,6-bis(4-phen-1-yloxy) (i.e., —$OPh(CH_2)_6PhO$—), 4-hydroxymethylphen-1-yl (i.e., 4-$HOCH_2Ph$—), 4-mercaptomethylphen-1-yl (i.e., 4-$HSCH_2Ph$—), 4-methylthiophen-1-yl (i.e., 4-$CH_3SPh$—), 3-methoxyphen-1-yl, 2-methoxycarbonylphen-1-yloxy (e.g. methyl salicyl), 2-nitromethylphen-1-yl (i.e., 2-$NO_2CH_2Ph$), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is an cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —$C_6H_{10}C(CF_3)_2C_6H_{10}O$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., $CH_3CHBrCH_2C_6H_{10}O$—), and the like. Further examples of cycloaliphatic radicals include 4-allyloxycyclohex-1-yl, 4-aminocyclohex-1-yl (i.e., $H_2C_6H_{10}O$—), 4-aminocarbonylcyclopent-1-yl (i.e., $NH_2COC_5H_8$—), 4-acetyloxycyclohex-1-yl, 2,2-dicyanoisopropylidenebis(cyclohex-4-yloxy) (i.e., —$OC_6H_{10}C(CN)_2C_6H_{10}O$—), 3-methylcyclohex-1-yl, methylenebis(cyclohex-4-yloxy) (i.e., —$OC_6H_{10}CH_2C_6H_{10}O$—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —$OC_6H_{10}(CH_2)_6C_6H_{10}O$—), 4-hydroxymethylcyclohex-1-yl (i.e., 4-$HOCH_2C_6H_{10}$—), 4-mercaptomethylcyclohex-1-yl (i.e., 4-$HSCH_2C_6H_{10}$—), 4-methylthiocyclohex-1-yl (i.e., 4-$CH_3SC_6H_{10}$—), 4-methoxycyclohex-1-yl, 2-methoxycarbonylcyclohex-1-yloxy (2-$CH_3OCOC_6H_{10}O$—), 4-nitromethylcyclohex-1-yl (i.e., $NO_2CH_2C_6H_{10}O$—), 3-trimethylsilylcyclohex-1-yl, 2-t-butyldimethylsilylcyclopent-1-yl, 4-trimethoxysilylethylcyclohex-1-yl (e.g. $(CH_3O)_3SiCH_2CH_2C_6H_{10}$—), 4-vinylcyclohexen-1-yl, vinylidenebis(cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" organic radicals substituted with a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g. —$CH_2CHBrCH_2$—), and the like. Further examples of aliphatic radicals include allyl, aminocarbonyl (i.e., —$CONH_2$), carbonyl, 2,2-dicyanoisopropylidene (i.e., —$CH_2C(CN)_2CH_2$—), methyl (i.e., —$CH_3$), methylene (i.e., —$CH_2$—), ethyl, ethylene, formyl (i.e. —CHO), hexyl, hexamethylene, hydroxymethyl (i.e. —$CH_2OH$), mercaptomethyl (i.e., —$CH_2SH$), methylthio (i.e., —$SCH_3$), methylthiomethyl (i.e., —$CH_2SCH_3$), methoxy, methoxycarbonyl (i.e., $CH_3OCO$—), nitromethyl (i.e., —$CH_2NO_2$), thiocarbonyl, trimethylsilyl (i.e. $(CH_3)_3Si$—), t-butyldimethylsilyl, 3-trimethyoxysilylpropyl (i.e., $(CH_3O)_3SiCH_2CH_2CH_2$—), vinyl, vinylidene, and the like. By way of further example, a $C_1$-$C_{10}$ aliphatic radical contains at least one but no more than 10 carbon atoms. A methyl group (i.e., $CH_3$—) is an example of a $C_1$ aliphatic radical. A decyl group (i.e., $CH_3(CH_2)_9$—) is an example of a $C_{10}$ aliphatic radical.

In the context of the present invention, alkyl is intended to include linear, branched, or cyclic hydrocarbon structures and combinations thereof, including lower alkyl and higher alkyl. Preferred alkyl groups are those of $C_{20}$ or below. Lower alkyl refers to alkyl groups of from 1 to 6 carbon atoms, preferably from 1 to 4 carbon atoms, and includes methyl, ethyl, n-propyl, isopropyl, and n-, s- and t-butyl. Higher alkyl refers to alkyl groups having seven or more carbon atoms, preferably 7-20 carbon atoms, and includes n-, s- and t-heptyl, octyl, and dodecyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl. Alkenyl and alkynyl refer to alkyl groups wherein two or more hydrogen atoms are replaced by a double or triple bond, respectively.

Aryl and heteroaryl mean a 5- or 6-membered aromatic or heteroaromatic ring containing 0-3 heteroatoms selected from nitrogen, oxygen or sulfur; a bicyclic 9- or 10-membered aromatic or heteroaromatic ring system containing 0-3 heteroatoms selected from nitrogen, oxygen or sulfur; or a tricyclic 13- or 14-membered aromatic or heteroaromatic ring system containing 0-3 heteroatoms selected from nitrogen, oxygen or sulfur. The aromatic 6- to 14-membered carbocyclic rings include, for example, benzene, naphthalene, indane, tetralin, and fluorene; and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl and phenethyl. Heteroarylalkyl means an alkyl residue attached to a heteroaryl ring. Examples include pyridinylmethyl and pyrimidinylethyl. Alkylaryl means an aryl residue having one or more alkyl groups attached thereto. Examples are tolyl and mesityl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, and cyclohexyloxy. Lower alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, and benzyloxycarbonyl. Lower-acyl refers to groups containing one to four carbons.

Heterocycle means a cycloalkyl or aryl residue in which one to two of the carbons is replaced by a heteroatom such as oxygen, nitrogen or sulfur. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, and tetrahydrofuran.

Substituted refers to residues, including, but not limited to, alkyl, alkylaryl, aryl, arylalkyl, and heteroaryl, wherein up to three H atoms of the residue are replaced with lower alkyl, substituted alkyl, aryl, substituted aryl, haloalkyl, alkoxy, carbonyl, carboxy, carboxalkoxy, carboxamido, acyloxy, amidino, nitro, halo, hydroxy, $OCH(COOH)_2$, cyano, primary amino, secondary amino, acylamino, alkylthio, sulfoxide, sulfone, phenyl, benzyl, phenoxy, benzyloxy, heteroaryl, or heteroaryloxy.

Haloalkyl refers to an alkyl residue, wherein one or more H atoms are replaced by halogen atoms; the term haloalkyl includes perhaloalkyl. Examples of haloalkyl groups that fall within the scope of the invention include $CH_2F$, $CHF_2$, and $CF_3$.

Many of the compounds described herein may contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as, their racemic and optically pure forms. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

Oxaalkyl refers to an alkyl residue in which one or more carbons have been replaced by oxygen. It is attached to the parent structure through an alkyl residue. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

Silyl means an alkyl residue in which one to three of the carbons is replaced by tetravalent silicon and which is attached to the parent structure through a silicon atom. Siloxy is an alkoxy residue in which both of the carbons are replaced by tetravalent silicon that is endcapped with an alkyl residue, aryl residue or a cycloalkyl residue, and which is attached to the parent structure through an oxygen atom.

A bidentate ligand is a ligand that is capable of binding to metals through two sites. Similarly, a tridentate ligand is a ligand that is capable of binding to metals through three sites. Cyclometallated ligand means a bidentate or tridentate ligand bound to a metal atom by a carbon-metal single bond and one or two metal-heteroatom bonds, forming a cyclic structure, wherein the heteroatom may be N, S, P, As, or O.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

EXAMPLES

Chemicals and Reagents

Chemicals and reagents are obtained from Aldrich. Flash chromatography was carried out by Fisher Scientific (100-200 mesh) or Aldrich (60-350 mesh) silica gel, prepacked silica gel column by Isco. Thin layer chromatography was carried out on commercially available pre-coated glass plates (Analtech, GF, 250 microns).

General Methods

Molecular weights were determined relative to polystyrene standards on a Perkin Elmer Series 200 GPC equipped with a Polymer Laboratories size exclusion column (PLgel 5 μm MIXED-C, 300×7.5 mm kept at 40° C.) using chloroform with 3.6% v/v isopropanol as the mobile phase. NMR spectra were measured on a Bruker 400 or Bruker Advance 500 spectrometers.

Synthesis

The synthesis of the N-(1,3-resorcinol)carbazole and N-hydroquinone carbazole was done in a two-step process as shown in scheme 1, addition of bromo-dimethoxy benzene to carbazole followed by deprotecting the methoxy group to give rise to the dihydroxy compound. N-Arylation can be achieved by Pd catalyzed procedures or use CuI as the catalyst. Condensation polymerization were synthesized by typical procedures.

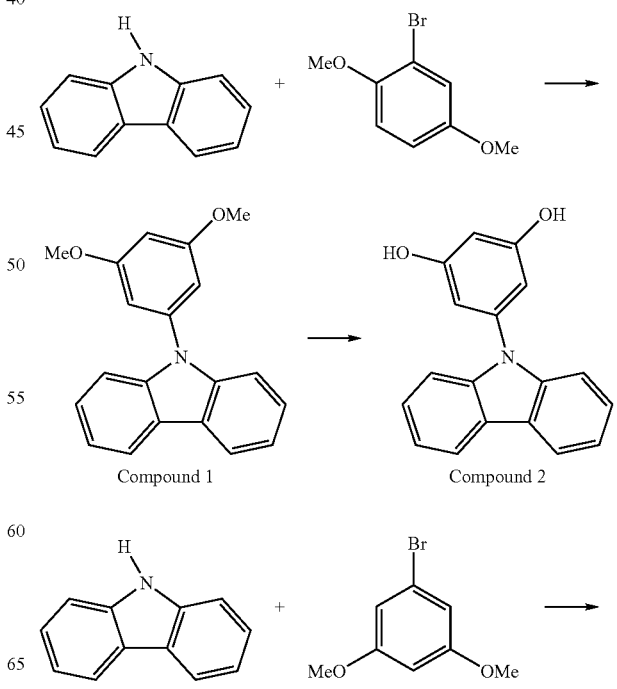

-continued

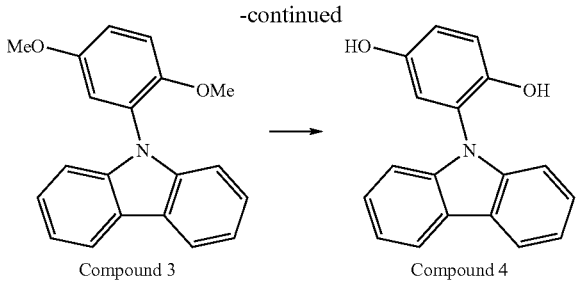

Compound 3  Compound 4

Example 1

Synthesis of Compound 1 9-(3,5-dimethoxyphenyl)-carbazole

To a three neck round bottom flask, was charged bromo-3,5-dimethoxybenzene (1.54 g, 7.1 mmol), carbazole (1.186 g, 7.1 mmol), potassium phosphate (3 g, 14.2 mmol) and copper iodide (0.14 g, 0.7 mmol). Dioxane (40 ml) was added and the reaction flask. The flask was evacuated and flushed with argon. Dimethylethylene diamine (0.14 g, 1.6 mmol) was then added to the reaction flask under a strong purge of argon. The reaction mixture was then heated at 95° C. for 48 h under argon. The reaction was followed by TLC. After the reaction was complete, the solution was cooled down to room temperature, and 10 mL of $H_2O$ was added. The reaction mixture was extracted with methylene chloride and the organic and aqueous phases were separated. The organic phase was further washed twice with 100 mL of water (×2) and once with 100 mL of brine (×1) and dried over $Na_2SO_4$. After solvent removal under vacuo, afforded crude product. Crude product was dissolved in $CH_2Cl_2$ and hexanes were added until the colored residues precipitated out. The solution was filtered to remove the colored residues. The mother liquor was concentrated to afford 1.0 g (46.5%) of light yellow oil as the product. $^1$H NMR ($CDCl_3$) δ 7.98 (d, 2H), 7.35 (d, 2H), 7.23 (d, 2H), 7.11 (t, 2H), 6.6 (s, 2H), 6.43 (s, 1H), 3.65 (s, 6H). EI-MS: 303(M+).

Example 2

Synthesis of Compound 2 9-(3,5-hydroxyphenyl)-carbazole

In a 500 mL round bottom flask equipped with a stir bar, 31.3 g of compound 1 (103 mmol) was added to a 200 mL of anhydrous $CH_2Cl_2$. Solution was cooled in a dry ice-acetone bath. Boron tribromide (180 mmol, 180 mL of 1M solution in $CH_2Cl_2$) was added via syringe drop wise to the solution. The flask was further chilled in the dry ice bath and allowed to equilibrate to room temperature overnight. After the reaction was complete, the solution was decanted into 100 mL of ice water while stirring. After 30 minutes of hydrolysis, the organic layer was extracted twice with 200 mL of $CH_2Cl_2$. The organic layer was then washed twice with 200 mL of cold water to neutralize any excess $BBr_3$. Solution was dried with sodium sulfate and the solvent was evaporated using a rotary evaporator to give the crude product. Recrystallization from THF/hexanes afforded 12.74 g (44.98%) of product that was then subsequently used for polymerization reactions. $^1$H NMR ($CDCl_3$) δ 8.15 (d, 2H), 7.52 (d, 2H), 7.44 (t, 2H), 7.32 (t, 2H), 6.66 (s, 2H), 6.47 (s, 1H).

Example 3

Synthesis of Compound 3 9-(2,5-dimethoxyphenyl)-carbazole

The procedure described in Example 1 was followed here using the bromo-2,5-dimethoxybenzene as one of the reactants.

Example 4

Synthesis of 9-(2,5-hydroxyphenyl)-carbazole (Compound 3)

The procedure described in Example 2 was followed using compound 3 as the starting material.

Example 5

Polymerization of Compound 2 with Terephthaloyl dichloride 0.3969 g (1.441 mmol) of compound 2 and 0.2956 g (1.456 mmol) of 1,4-terephthaloyl dichloride and 4 mL of anhydrous $CHCl_3$ was charged into a dry round bottom flask with a magnetic stirring bar under nitrogen atmosphere. The resulting milky solution was immersed in an ice-salt bath for 15 min and then 0.533 mL of dry triethylamine was added using a syringe. Solution became clear immediately. The mixture was maintained at 0-5° C. with stirring for 1 h, allowed to warm to room temperature, and stirred for additional hour. Then, 0.0032 g of cumylphenol was added. Then the mixture was diluted with 5 mL of $CH_2Cl_2$, and washed successively twice with equal volumes of 1 N HCl and water. The solution was precipitated into 40 mL of methanol. The collected polymer was redissolved in 10 mL of $CH_2Cl_2$ and this solution was added slowly to 100 mL of boiling, deionized water. The solids were again collected, air-dried, redissolved in fresh $CH_2Cl_2$ (4 mL) and reprecipitated into methanol. The resulting polymer (0.3747 g) was dried at 80° C. in a vacuum oven overnight. GPC analysis indicated that the polymer has weight average molecular weight Mw of 4241, and a polydispersity index PDI of 1.61.

Example 6

Polymerization of Compound 2 with Bisphenol A Bischloroformate

A dry reaction vessel equipped with a magnetic stirring bar under nitrogen atmosphere, was charged with the compound 2 (0.2750 g, 1 mmol), BPA-bischloroformate (0.353 g, 1 mmol), and 4 mL of dry $CH_2Cl_2$. The resulting milky solution was immersed in an ice-salt bath for 15 min and then charged with 0.37 mL of dry triethylamine. Solution immediately became clear. The mixture was maintained at 0-5° C. with stirring for 1 h, allowed to warm to room temperature, and stirred overnight. Then the mixture was diluted with 10 mL of $CH_2Cl_2$, 15 mL of 10% NaHCO3 was added, and the mixture was stirred for 10 min and then transferred to a separatory funnel. The aqueous phase was discarded and the organic phase was washed successively with equal volumes of 1 N HCl once and water twice. Then solution was precipitated into 40 mL of methanol. The collected polymer was redissolved in 10 mL of $CH_2Cl_2$ and this solution was added slowly to 1000 mL of boiling, deionized water. The solids were again collected, air-dried, redissolved in fresh $CH_2Cl_2$ (12 mL) and reprecipitated again into methanol. The resulting polymer (0.26 g) was dried at 80° C. in a vacuum oven overnight. GPC analysis indicated that the polymer has weight average molecular weight Mw of 7362, and a polydispersity index PDI of 1.68.

Example 7

Polymerization of Compound 2 with Difluorodiphenylsulfone 0.5506 g (20 mmol) of compound 2 and 0.4146 g of $K_2CO_3$ were placed 50 mL of three neck round bottom flask was charged with 7 mL of DMAc and 4 mL of toluene. The reaction flask was equipped with an overhead stirrer and a Dean-stark trap. Reaction mixture was heated to 130° C. to remove toluene. After all toluene was removed, difluorodiphenylsulfone (0.5085 g, 20 mmol) was added along with 4 mL of toluene. Toluene distillation continued. After all the toluene was removed, reaction temperature was increased to 150° C. After 4 hours, reaction was stopped and the reaction mixture was precipitated into methanol (1:10 v/v ratio). The powder was collected and redissolved in 10 mL of $CHCl_3$ and precipitated into methanol. Collected 110 mg of powder. GPC analysis indicated that the polymer has weight average molecular weight Mw of 4103, and a polydispersity index PDI of 1.26.

General Procedure for Life Time Decay Measurements:

The lifetime of triplet excited states were measured using an Edinburgh CD920 spectrometer equipped with a cooled R928 photo multiplier tube. The typical procedure was to place a sample in a vacuum dewer and then pump down to $4*10E^{-5}$ torr. Then the sample was optically excited at 394 nm with a pulsed diode laser (class HIB, 390-420 nm, maximum power of 5 mW). Time resolved emission spectra were measured at 470 nm. Polystyrene (PS) used in this work was GPC standard Mw=18,700 obtained from Aldrich and used as received. Poly(9-vinylcarbazole) (PVK), Mw~1,100,000, was obtained from Aldrich. Iridium (III) bis(2-(4,6-difluorephenyl)pyridinato-N, $C^2$) (FIrpic) was obtained from American Dye Sources, Inc. Quebec, Canada.

Sample preparation: Samples for this experiment were prepared in the following manner:

Example 8

A mixture of 1 wt % FIrpic in PS was prepared by mixing 0.020 ml of 0.5 wt % FIrpic (10 mg of FIrpic in 2 ml THF) with 1.0 ml of 1 wt % PS in THF. A thin film sample [PS: FIrpic] was obtained by spin-coating the solution onto a pre-cleaned quartz substrate.

Example 9

A mixture of 1 wt % FIrpic in polymer from Example 6 was prepared by mixing 0.020 ml of 0.5 wt % FIrpic (10 mg of FIrpic in 1 ml THF) with 1.0 ml of 1 wt % 62-90 (10 mg of 62-90 in 1 ml THF). A thin film sample was obtained by spin-coating the solution onto a pre-cleaned quartz substrate.

Comparative Example 1

A mixture of 1 wt % FIrpic in Poly(N-vinyl carbazole) was prepared by mixing 0.020 ml of 0.5 wt % (10 mg of FIrpic in 1 ml THF) with 1.0 ml of 1 wt % PVK in THF. A thin film sample was obtained by spin-coating the solution onto a pre-cleaned quartz substrate.

FIG. 1 shows the time resolved photoluminescence spectra of the device comprising the copolycarbonate from Example 6, and that of the device comprising polystyrene. The phosphorescent dye FIrpic had comparable triplet decay profiles (or equivalently decay lifetimes) when dispersed in the copolycarbonate of Example 6 (dotted line) relative to the insulating polystyrene (solid line), indicating that there is no energy back transfer from the dye FIrpic to the polymer host. Thus, polymer of the invention is suitable as a host material for FIrpic in blue phosphorescent OLEDs. FIG. 2 shows the time resolved photoluminescence spectra of device comprising poly(N-vinyl carbazole) and that of the device comprising polystyrene. The spectra from the device comprising poly(N-vinyl carbazole) (dotted line) exhibited a much faster decay profile than the device comprising polystyrene (solid line), indicating that there is energy back transfer from FIrpic to poly(N-vinyl carbazole).

Examples 10 and 11

Synthesis of Polymer-Bound Dye

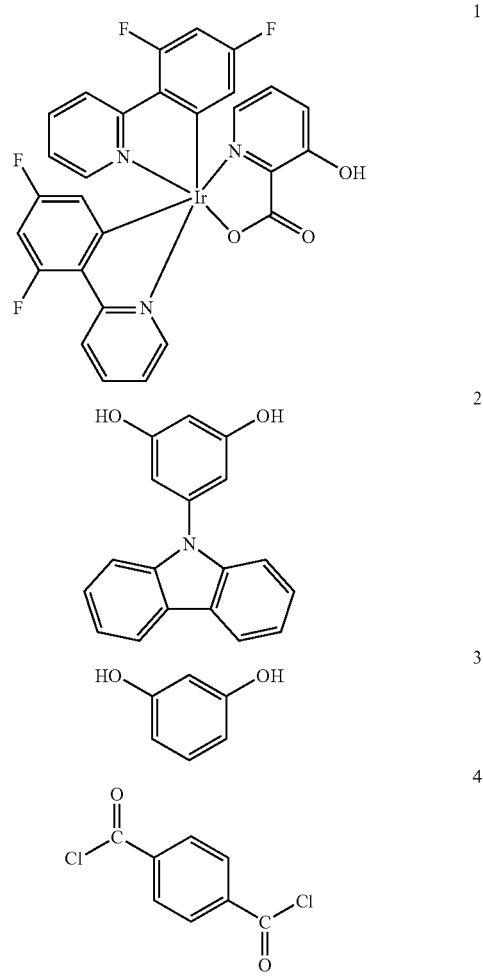

Example 10

Synthesis of Polyester-Bound Dye

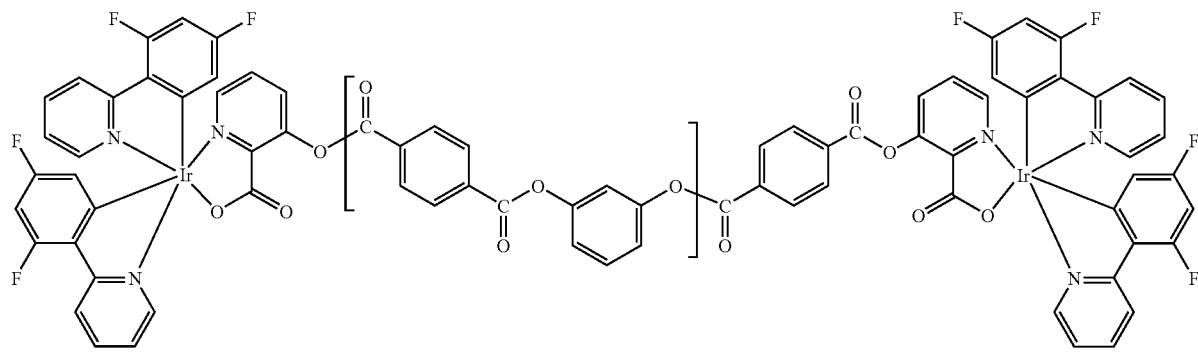

Mw = 2864
PDI = 1.34

To a dry 25 mL dried three-neck round bottom flask was added 0.05628 g (0.095 mmol) of phenol FIrpic derivative (1) along with 0.2505 g (1.234 mmol) terephthaloyl chloride (4), then 5 mL of dry $CHCl_3$ was added. The suspension was purged under $N_2$, and chilled in an ice-salt water bath for 10 min. To this solution, 0.45 mL of dry triethylamine (TEA) was added using a syringe in a dropwise manner. Upon the addition of TEA, the milky solution started to become clear. The solution was stirred at ice water temperature for an hour, then warmed to room temperature overnight under $N_2$. The solution was diluted with $CHCl_3$ (10 mL) the next day, then washed with equal amounts of $NaHCO_3$ and water three times. The solution was concentrated into 3 mL and anti-solvent precipitated into 50 mL of methanol. The polymer was collected by filtering through M-sized fritted filter. Mw=2864, PDI 1.34.

Example 11

Synthesis of Dye Bound to Carbazole-Functional Polyester

To a dry 25 mL dried three-neck round bottom flask was added 0.3320 g (1.206 mmol) carbazole resorcinol (2), 0.06748 g (0.095 mmol) of phenol FIrpic derivative (1) along with 0.2545 g (1.253 mmol) terephthaloyl chloride (4), then 11 mL of dry $CHCl_3$ was added. The suspension was purged under $N_2$, and chilled in a ice salt water bath for 10 min. To this solution, 0.45 mL of dry triethylamine was added using a syringe in a drop wise. Upon the addition of TEA, the milky solution started to become clear. The solution was stirred at ice water temperature for an hour then warmed to room temperature overnight under $N_2$. The solution was diluted with $CHCl_3$ (22 mL) the next day, then washed with equal amounts of $NaHCO_3$ and water three times. The solution was concentrated into 7 mL and anti-solvent precipitated into 50 mL of methanol. The polymer was collected by filtering through M-sized fritted filter. Mw=5093, PDI=1.34.

Example 12

Multilayer OLED Fabrication Via Differential Solubility

The materials were soluble in 1,1,1,3,3,3-hexafluoro-2-propanol (HFIP) and could thus be solution-processed; the materials were insoluble in other organic solvents (such as toluene, xylene and chlorobenzene etc) commonly used in

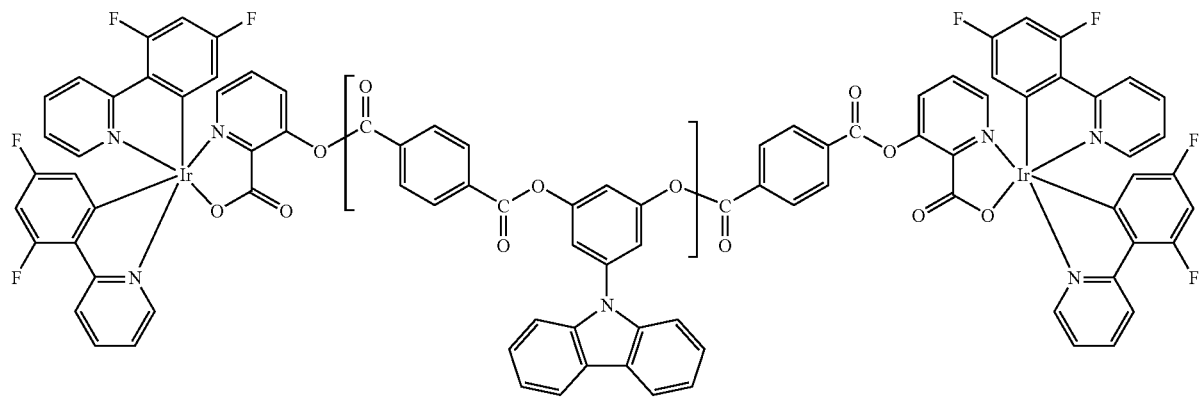

Mw = 5093
PDI = 1.34 making POLEDs, thus allowing sequential application of other electro-active layers on top of a pre-deposited resorcinol-based material.

Washing Off Test:

Solution preparation: The polymer of Example 10 (6.5 mg) was dissolved in HFIP (0.65 milliliter) to give a clear solution Film preparation: The solution was spin-coated in air (RT=24° C. and RH=32%) on a precleaned quartz substrate, and then baked at 70° C. for 10 min in a glovebox with less than 1 ppm oxygen and moisture. Photoluminescence (PL) spectrum of the film was measured with an Edinburgh Spectrometer (excitation at 370 nm), then the film was rinsed with toluene. The PL spectrum was measured, the film was rinsed with THF; and the PL spectrum was measured again. The material emitted sky blue light characteristic of FIrpic upon excitation at 370 nm. Rinsing the film with toluene did not cause significant change in PL intensity (or no significant change in film thickness), suggesting that the material was at least partially insoluable in toluene. Rinsing the film with THF resulted in a slight reduction in PL intensity/film thickness.

The invention claimed is:

1. A condensation polymer selected from the group consisting of polyesters, polycarbonates, polyetherimides, polyaryletherketones, polyarylethersulfones and polyestercarbonates comprising structural units derived from a polymerizable phosphorescent organometallic compound of formula

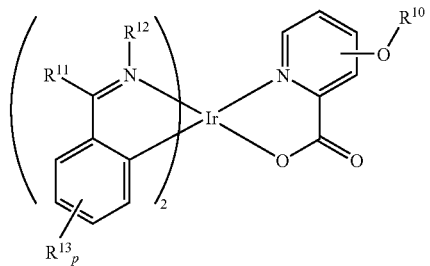

wherein $R^{10}$ is hydrogen, alkoxy substituted with at least one hydroxy group, aryl substituted with at least one hydroxy group, alkylaryl substituted with at least one hydroxy group, arylalkyl substituted with at least one hydroxy group, or a combination thereof;

$R^{11}$ and $R^{12}$ taken together form a substituted or unsubstituted monocyclic or bicyclic heteroaromatic ring;

$R^{13}$ is independently at each occurrence halo, nitro, hydroxy, amino, alkyl, aryl, arylalkyl, alkoxy, substituted alkoxy, substituted alkyl, substituted aryl, or substituted arylalkyl; and p is 0, or an integer ranging from 1 to 4.

2. A condensation polymer according to claim 1, wherein M is Ir.

3. A condensation polymer according to claim 1, wherein the polymerizable phosphorescent organometallic compound is a picolinate.

4. A condensation polymer according to claim 1, which is a polyester.

5. A condensation polymer according to claim 1, wherein the polymerizable phosphorescent organometallic compound is indium(III)-bis[2-(4,6-difluorophenyl)pyridinato-N,C$^{2'}$] picolinate.

6. A condensation polymer according to claim 1, of the formula

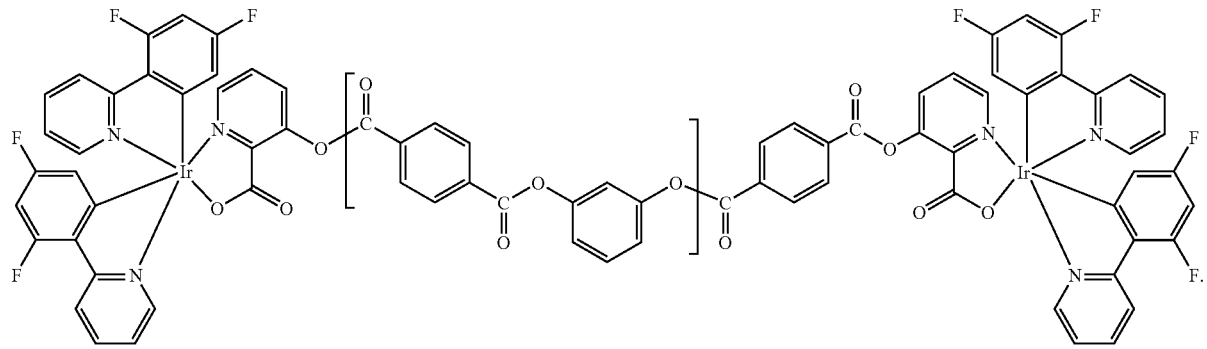

7. An optoelectronic device comprising a condensation polymer according to claim 1.

8. A condensation polymer selected from the group consisting of polyesters, polycarbonates, polyetherimides, polyaryletherketones, polyarylethersulfones and polyestercarbonates comprising structural units derived from a polymerizable phosphorescent organometallic compound of formula L'$_2$MZ' and structural units of formula II

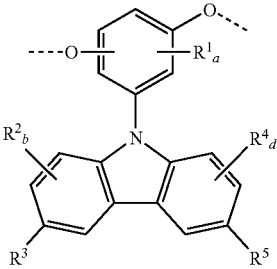

wherein

L' and Z' are independently bidentate ligands;

at least one of L' and Z' comprises at least one substituent selected from hydroxy, alkoxy substituted with at least one hydroxy group, aryloxy substituted with at least one hydroxy group, alkylaryloxy substituted with at least one hydroxy group, arylalkyloxy substituted with at least one hydroxy group, and combinations thereof;

M is Ga, Al, Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Ga, Ge, In, Sn, Sb, Tl, Pb, Bi, Eu, Tb, La, Po, or a combination thereof;

$R^1$, $R^2$, and $R^4$ are independently at each occurrence a $C_1$-$C_{20}$ aliphatic radical, a $C_3$-$C_{20}$ aromatic radical, or a $C_3$-$C_{20}$ cycloaliphatic radical;

wherein $R^3$ and $R^5$ are independently selected from the group consisting of hydrogen, triphenylsilyl, t-butyl, mesityl, diphenyl phosphine oxide, and diphenyl phosphine sulfide; and a, b and d are independently 0 or an integer ranging from 1 to 3.

9. A condensation polymer according to claim 8, comprising structural units of formula

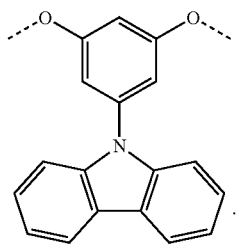

10. A condensation polymer according to claim 8, comprising structural units of formula

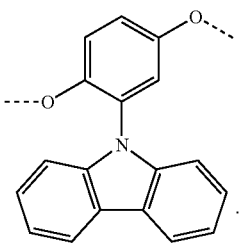

11. A condensation polymer according to claim 8, additionally comprising structural units of formula

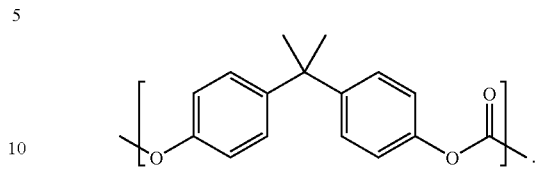

12. A condensation polymer according to claim 8, additionally comprising structural units of formula

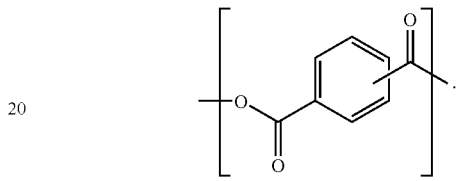

13. A condensation polymer according to claim 8, of formula

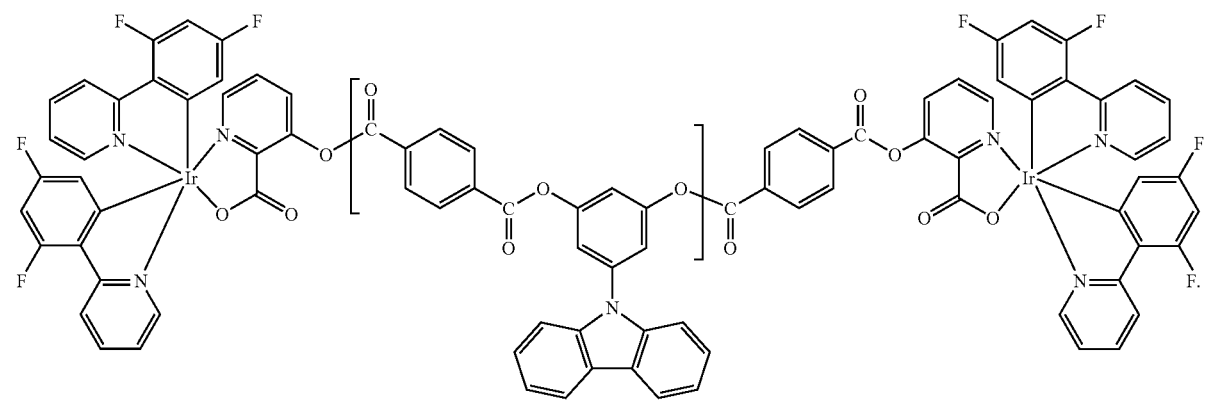

14. An optoelectronic device comprising a condensation polymer according to claim 8.

* * * * *

UNITED STATES PATENT AND TRADEMARK OFFICE
CERTIFICATE OF CORRECTION

PATENT NO.        : 7,851,579 B2
APPLICATION NO.   : 11/764852
DATED             : December 14, 2010
INVENTOR(S)       : Ye et al.

It is certified that error appears in the above-identified patent and that said Letters Patent is hereby corrected as shown below:

In Column 6, Lines 35-40, delete " 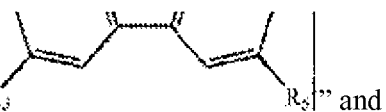 " and insert -- 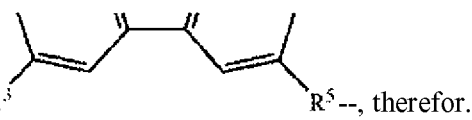 --, therefor.

In Column 9, Line 5, delete " 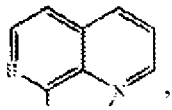 " and insert --  --, therefor.

In Column 15, Line 45, delete "isothphalic" and insert -- isophthalic --, therefor.

In Column 15, Line 62, delete "isothphalic" and insert -- isophthalic --, therefor.

In Column 16, Line 3, delete "isothphalic" and insert -- isophthalic --, therefor.

In Column 17, Line 38, delete "laers." and insert -- layers. --, therefor.

In Column 18, Line 49, delete "lanthamide" and insert -- lanthanide --, therefor.

In Column 21, Line 15, delete "$H_{10}O$-)," and insert -- $H_{10}$-), --, therefor.

In Column 26, Line 36, delete "and washed" and insert -- and was washed --, therefor.

In Column 32, Line 8, in Claim 5, delete "indium" and insert -- iridium --, therefor.

Signed and Sealed this
Twelfth Day of April, 2011

David J. Kappos
*Director of the United States Patent and Trademark Office*